United States Patent
Orazem

(10) Patent No.: US 8,310,251 B2
(45) Date of Patent: Nov. 13, 2012

(54) SYSTEM FOR ASSESSING PIPELINE CONDITION

(75) Inventor: Mark E. Orazem, Gainesville, FL (US)

(73) Assignee: University of Florida Research Foundation, Inc., Gainesville, GA (US)

( * ) Notice: Subject to any disclaimer, the term of this patent is extended or adjusted under 35 U.S.C. 154(b) by 510 days.

(21) Appl. No.: 12/522,126

(22) PCT Filed: Jan. 3, 2008

(86) PCT No.: PCT/US2008/050063
§ 371 (c)(1),
(2), (4) Date: Oct. 27, 2009

(87) PCT Pub. No.: WO2008/083409
PCT Pub. Date: Jul. 10, 2008

(65) Prior Publication Data
US 2010/0039127 A1 Feb. 18, 2010

Related U.S. Application Data

(60) Provisional application No. 60/883,273, filed on Jan. 3, 2007.

(51) Int. Cl.
*G01R 27/08* (2006.01)
(52) U.S. Cl. .................................... 324/713
(58) Field of Classification Search .......... None
See application file for complete search history.

(56) References Cited

U.S. PATENT DOCUMENTS

| | | | |
|---|---|---|---|
| 4,591,792 A * | 5/1986 | Birchmeier et al. | 324/425 |
| 4,658,365 A | 4/1987 | Syrett et al. | |
| 5,087,873 A * | 2/1992 | Murphy et al. | 205/775.5 |
| 5,126,654 A | 6/1992 | Murphy et al. | |
| 5,331,286 A | 7/1994 | Rivola et al. | |
| 5,445,719 A * | 8/1995 | Boiko | 205/776.5 |

(Continued)

FOREIGN PATENT DOCUMENTS

CN 1587785 A 3/2005

(Continued)

OTHER PUBLICATIONS

Souto, et al., "Accelerated Tests for the Evaluation of the Corrosion Performance of Coil-Coated Steel Sheet", Progress in Organic Coatings, vol. 53, No. 1, May 1, 2005.

(Continued)

*Primary Examiner* — Paresh Patel
(74) *Attorney, Agent, or Firm* — Thomas Horstemeyer

(57) ABSTRACT

A method and system for assessment of a pipe (110) is provided. The system can include a probe (100) having first (120) and second (130) electrodes and a processor (200) in communication with the probe (100). The probe (100) can be in a medium (140) proximate to a section of the pipe (110) to be analyzed. The section of the pipe (110) can have a coating (115) thereon. The processor (200) can measure a difference in potential between the first (120) and second (130) electrodes. The processor (200) can determine a local impedance with respect to the section of the pipe (110) based at least in part on the difference in potential. The processor (200) can evaluate a condition of the coating (115) on the section of the pipe (110) based at least in part on the local impedance or a parameter derived from the local impedance.

17 Claims, 8 Drawing Sheets

U.S. PATENT DOCUMENTS

| | | | |
|---|---|---|---|
| 5,674,375 | A | 10/1997 | Thompson |
| 6,107,811 | A | 8/2000 | Caudill et al. |
| 6,171,025 | B1 | 1/2001 | Langner et al. |
| 6,262,578 | B1 | 7/2001 | Hudson |
| 6,264,824 | B1 | 7/2001 | Reid et al. |
| 6,577,144 | B2 | 6/2003 | Vail, III et al. |
| 6,582,587 | B1 * | 6/2003 | Srinivasan et al. ............ 205/724 |
| 6,727,695 | B2 | 4/2004 | Krivoi et al. |
| 6,919,729 | B2 | 7/2005 | Tiefnig |
| 2002/0078752 | A1 | 6/2002 | Braunling et al. |
| 2003/0074162 | A1 | 4/2003 | Fourie et al. |
| 2003/0101804 | A1 | 6/2003 | Zanker |
| 2003/0136195 | A1 | 7/2003 | Krieg et al. |
| 2003/0169058 | A1 | 9/2003 | Pierre et al. |
| 2005/0145018 | A1 | 7/2005 | Sabata et al. |

FOREIGN PATENT DOCUMENTS

| | | |
|---|---|---|
| MX | PA01009030 A | 4/2002 |
| NL | 1015354 C2 | 1/2001 |
| WO | 2004074808 A2 | 9/2004 |

OTHER PUBLICATIONS

Srinivasan, R, Murphy, "Corrosion Detection on Underground Gas Pipeline by Magentically Assisted AC Impedance," Corrosion 90/406, NACE.

Jankowski, Jesmar, "Monitoring Methods of Cathodic Protection of Pipelines," Gdansk University of Technology.

Dykmarova, et al., "On a Possibility of Determination of Underground Pipeline Corrosion State by Contactless Methods," IEEE International Workshop on Acquisition and Advanced Computing Systems: Technology and Applications, Sep. 2003.

Robers, et al., "Pulsed Eddy Current in Corrosion Detection," NDT. net, Oct. 2002, vol. 7 No. 10.

Wikswo, Jr., et al., "Magnetic Susceptibility Imaging for NonDestructive Evaluation," IEEE Transactions on Applied Superconductivity, vol. 3, No. 1, Mar. 1993.

Castaneda, et al., "Life Prediction Estimation of an Underground Pipeline Using Alternate Current Impedance and Reliability Analysis," Corrosion, vol. 60, No. 5, pp. 429-436, May 2004.

Hong, et al., "Monitoring Corrosion in Multiphase Pipelines," Materials and Corrosion, vol. 52, Issue 8, pp. 590-597, Aug. 17, 2001.

Hong, et al., "Effect of Oil in Multiphase Flow on Corrosion Product Film in Large Horizontal Pipeline," Materials and Corrosion, vol. 51, Issue 6, pp. 439-443, Jul. 6, 2000.

International Preliminary Report on Patentability, dated Jul. 16, 2009.

International Search Report and Written Opinion, dated Oct. 4, 2008.

Souto, et al., "Accelerated Tests for the Evaluation of the Corrosion Performance of Coil-Coated Steel Sheet: EIS Under Cathodic Polarisation," Progress in Organic Coatings, vol. 53, No. 1, May 1, 2005, pp. 71-76.

* cited by examiner

SYSTEM FOR ASSESSING PIPELINE CONDITION

CROSS-REFERENCE TO RELATED APPLICATIONS

This application is a §371 national stage entry of International Application No. PCT/US2008/050063, filed Jan. 3, 2008, which claims priority to U.S. Provisional Application No. 60/883,273, filed Jan. 3, 2007, all of which are hereby incorporated by reference.

TECHNICAL FIELD

The invention relates generally to methods and systems for detecting the condition of metallic pipes.

BACKGROUND ART

In the United States alone, over 1.3 million miles of buried steel main-line pipe are used for the transport of natural gas alone, many at high pressures on the order of 1000 psi. Trunk lines for natural gas products add to this total. There are also about 170,000 miles of pipeline for transport of crude oil and refined products. There are a significant number of pipeline failures reported each year with a few involving loss of life or significant property loss.

Corrosion of the pipe material is one of the main causes of pipeline failure. Corrosion is an electrochemical process involving metal oxidation of the pipe and mass and charge transport with an electrode via a surrounding electrolyte. The charge transport implies that an electrical current flows between locations on the pipe and from the pipe to one or more external electrodes. A metallic pipeline can become an electrode and the soil act as an electrolyte so that the pipeline buried in soil provides the elements of an electrolytic cell.

Some corrosion arises from the naturally occurring processes at specific locations on the pipe involving electrical current flow into the ambient soil electrolyte via the corrosion reaction. Corrosion can also be accelerated by voltages applied to a local region of the pipe by man-made structures, including local transit systems, power distribution systems and other terrestrial sources of stray voltages and currents.

Early detection and control of corrosion are necessary to maintain the integrity of a pipeline and reduce the likelihood of a pipeline failure. In order to reduce the likelihood of a pipeline failure, U.S. Federal Law requires that pipelines are periodically tested for indications of corrosion activity.

Electrical potential measurements are commonly used to assess the efficacy of corrosion prevention strategies. Buried oil and gas transmission pipelines are protected from corrosion by a combination of cathodic protection and coatings that reduce the current requirements for cathodic protection. Cathodic protection (CP) is a method of preventing metal corrosion by suppressing the electrochemical corrosion reaction. The metal being protected is forced to be a cathode by either impressing a small current upon it, or by placing it in electrical contact with a sacrificial anode, i.e. a metal that is more easily oxidized than the protected metal. These methods of CP are referred to as Impressed Current Cathodic Protection (ICCP) and Sacrificial Anode Cathodic Protection (SACP), respectively.

One of the advantages of CP is that it can provide protection without changing the immediate physical environment of the structure. By its nature, CP provides the correct electrochemical conditions to control the corrosion process without requiring full access to the material to be protected, thus preserving the visual appearance and structural integrity of the structure.

Regular inspections, such as described in the NACE (National Association of Corrosion Engineers) International Recommended Practice for External Corrosion Direct Assessment (ECDA), are required to ensure the integrity of the pipelines. The methodology behind ECDA relies heavily on close-interval surveys of on-potentials (where the CP system is connected) and off-potentials (where the CP system is disconnected).

The procedure used for a close-interval survey is to place a reference electrode in contact with the soil surface above the pipe and measure the electrical potential difference with respect to a connection to the pipe. Since it is impractical to connect to the pipe at each point where a measurement is taken, a length of wire is used to reach convenient connection points. The measurement location and electrical potential are recorded and the next measurement is taken. In some cases, the distance between measurements is the length of one pace of the person obtaining the data. In other cases, an A-frame is used to control more precisely the distance between potential readings.

One available system superimposes a single-frequency signal (937.5 Hz with a maximum output of 750 mA or 4 Hz with a maximum output of 3 A) on the current supplied for cathodic protection. A magnetometer, tuned to the imposed frequency, is used to measure the current flowing in the pipe. A discontinuity in the current is associated with coating flaws. Although such instruments can detect certain coating flaws, such systems can be insensitive to large coating flaws. Another available system applies an AC signal, containing many frequencies, to the pipe, and the corresponding current is detected at various locations using a magnetometer. The ratio of input potential and output current yields a frequency-dependent impedance. The magnetometers can be used as well to map the current distribution associated with application of cathodic protection.

However, magnetically-assisted impedance-based systems have not gained acceptance in the field. One factor inhibiting acceptance of the magnetically assisted impedance technique within the industry is that it requires depolarization of the pipeline because the magnetically-assisted impedance-based technique cannot be employed while the pipe is under cathodic protection. Even after the impressed current is removed from the pipe, depolarization may take hours. Additionally, interpretation of the impedance results requires a detailed electrical circuit model, which is unlikely to be correct, and requires low-frequency data, which takes a long time to collect. For example, a measurement of three 0.01 Hz (10 mHz) cycles requires 300 seconds. Accordingly, methods which provide measurement under normal operating conditions and provide more sensitivity for above ground assessment of the condition of buried pipe are desired.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION

Figure 1:
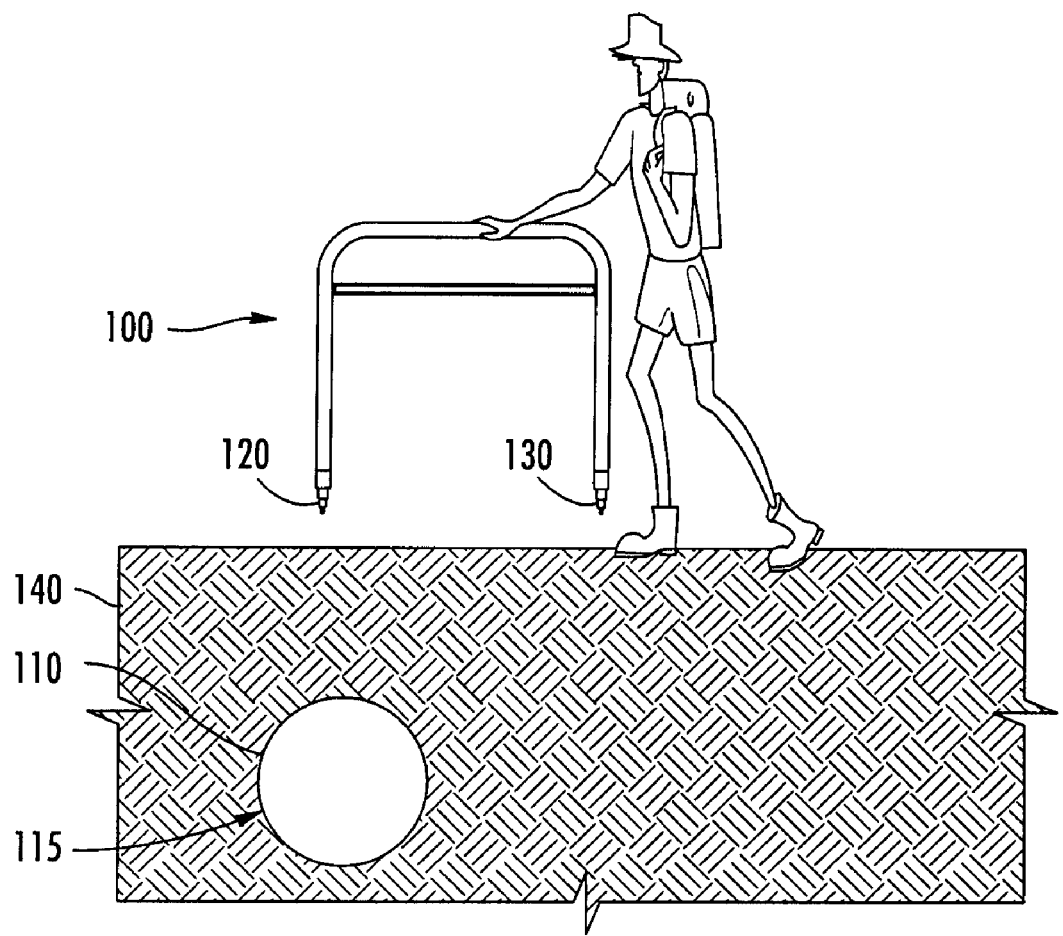
FIG. 1 is an arrangement of potential sensing reference electrodes on a portable A-frame device.

The invention comprises an apparatus and associated methods for above-ground assessment of the external condition of a pipe, such as a buried pipe. In one embodiment, the pipe can be under impressed current cathode protection (ICCP), even during the assessment measurements. In this embodiment, current is superimposed on the pipe section to be analyzed over current supplied for the ICCP. Alternatively, current can be injected into the pipe through a separate connection.

The method can comprise the steps of disposing a probe 100 having capability to sense electrical potential using a plurality of spaced apart electrodes 120, 130 in an electrolytic medium 140 (e.g. soil) proximate to a section of buried pipe 110 to be analyzed. In an exemplary two-electrode arrangement, the respective electrodes 120, 130 are referred to herein as a reference electrode 120, which is positioned closest to the pipe 110, and a second electrode 130, which is positioned further from the pipe 110 than the reference electrode 120. The difference in electrical potential between the reference electrode 120 (closest to the pipe) and second electrode 130 can be used to determine the local current density. This determination, described below, can utilize the numerical value of the soil 140 resistivity in the vicinity of the probe 100. The electrical potential difference between the pipe 110 metal and the reference electrode 120 closest to the pipe 110 can be measured while the system is subjected to an oscillatory current or potential signal. The ratio of the electrical potential difference and the local current density gives rise to a local impedance parameter which can be used to determine the condition of the pipe 110 and a coating 115 disposed thereon.

The pipe 110 section has an electrically insulating coating 115 on at least a portion, and generally on its exterior surface area along its entire length, except for defects 150 (FIG. 3) that may exist. The interface between the pipe 110 and the soil 140 is referred to herein as the "corrosion interface." It is this corrosion interface and its associated interfacial impedance, which are components of the local impedance as defined below, that can be utilized by in one or more of the exemplary embodiments of the present invention to assess the condition of the pipe 110, such as a coating 115 on a buried pipe 110. From the interfacial impedance, an interfacial capacitance can be determined which has been found to be indicative of the condition of the pipe coating 115.

The soil 140 resistivity can be known, estimated, or in a preferred embodiment determined. The resistivity can be determined by applying a potential difference between the respective electrodes 120, 130 and measuring the resulting current density, or by forcing or otherwise providing a current thereto and measuring the resulting potential. For example, a high-frequency oscillation forcing signal or a steady forcing signal may be used. The measurement can be repeated on a regular basis to allow for seasonal or weather-related changes in the resistivity of soil 140 or another electrolyte 140. As used herein, "high-frequency oscillation forcing signal" refers to a forcing signal with a frequency of about 1 Hz or greater, preferably about 100 Hz or greater, and more preferably about 500 Hz or greater. In a preferred embodiment, the high-frequency oscillation forcing signal can have a frequency within the range of 100-10,000 Hz.

The local impedance, being the total impedance between the pipe 110 section and one of the electrodes 120, 130, preferably the reference electrode 120 (closest electrode), can be determined by forcing an AC current or voltage at a plurality of different frequencies between the pipe 110 and one of the electrodes 120, 130. In one embodiment, the current can include at least two discrete frequencies, other than the CP frequency used to protect the pipe 110 using impressed current cathode protection (ICCP), which is normally 120 Hz (and full wave rectified).

The local impedance can be the series combination of the resistance of soil 140 or other electrolytes and the parallel combination of interfacial resistance and interfacial capacitance. Thus, the local impedance can include both a real component and an imaginary component.

Figure 5:
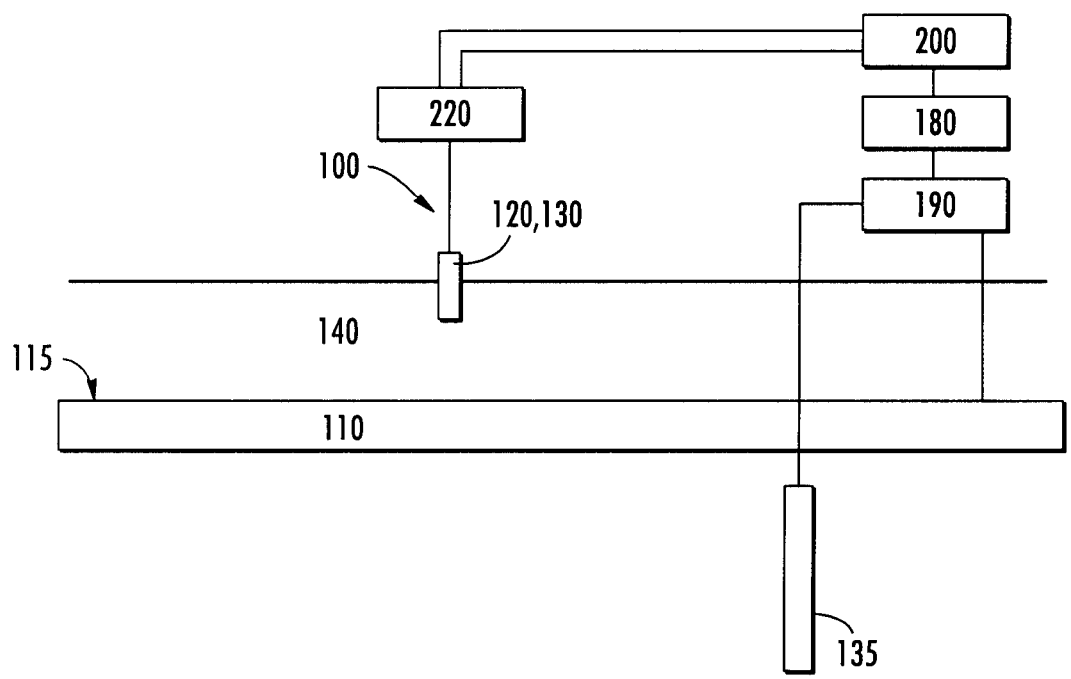
FIG. 5 is a schematic of a system of the present invention, including a device for superimposing a single or multi-sine current on an existing cathodic protection signal, and a device for analyzing local impedance.
Figure 6:
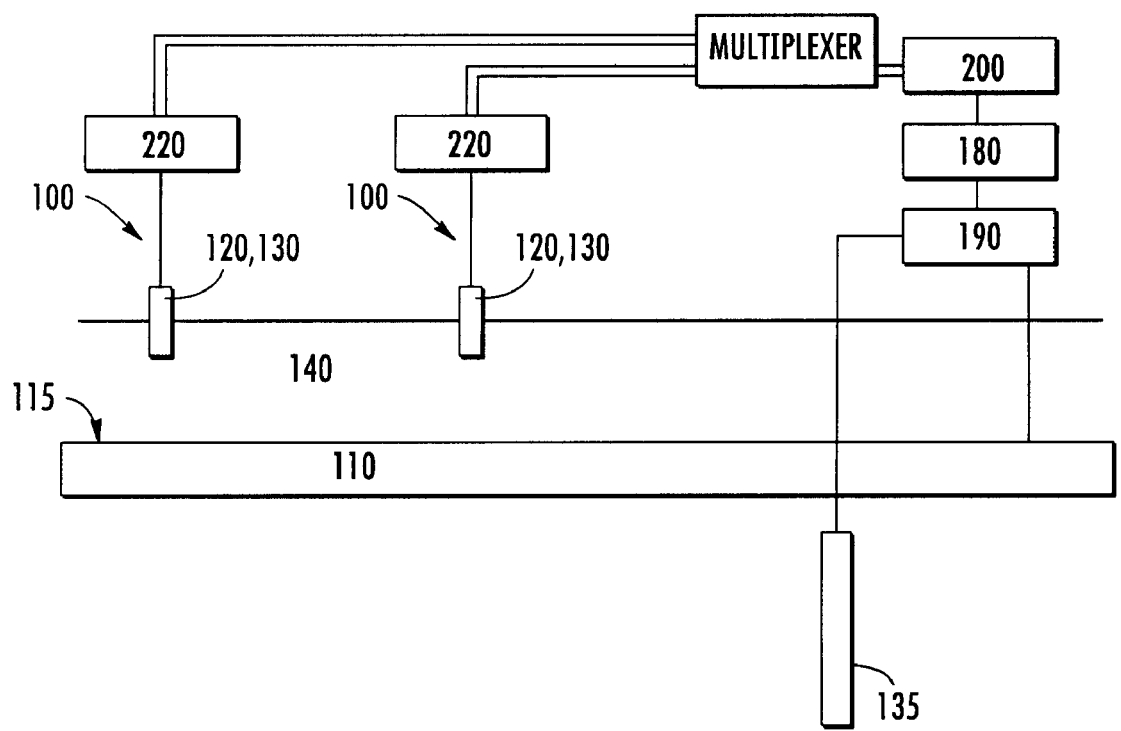
FIG. 6 is a schematic of a system of the present invention, including a device for superimposing a single or multi-sine current on an existing cathodic protection signal, and a device for analyzing impedance that includes several wired electrodes for measuring local impedance.

In a preferred embodiment, alternating current can be forced onto or otherwise provided to the pipe 110. The current imposed onto the pipe 110 can be conducted mainly along the horizontal length of the pipe 110. However, a distributed leakage current may flow from the pipe 110 into the soil 140 along the length of the pipe 110 and eventually return to the source through the electrode(s) 120, 130, as shown in FIGS. 5 & 6. The magnitude of the current loss from the pipe 110 at a selected position along the pipe 110 can depend primarily upon the condition of the protective, non-electrically conductive coating 115 on the pipe 110, and the frequency of the impressed signal. Some of this leakage current can reach the electrode 120, 130, thereby changing its electrical potential.

One method of making a reading according to the present invention can start with measuring the electrical potential (V) of the electrode 120, 130. As described above, the local interfacial impedance can then be obtained at several frequencies from the ratio of the potential measured (V) and the local current density.

A constant, $\alpha$, can then be determined as the ratio of the log of the magnitude of the imaginary component of the local impedance divided by the log of frequency in the limit as the frequency approaches infinity. A quantity related to the capacitance of the pipe, $Q_{eff}$, can then be calculated using the constant, $\alpha$. Pipe capacitance, $C_{pipe}$, can then be estimated from the quantity related to the capacitance (per unit area) of the pipe, $Q_{eff}$.

It has been discovered that high capacitance per unit area (e.g. about $10^{-5}$ F/cm$^2$) can be evidence of a coating 115 problem, while low capacitance (e.g. about $10^{-9}$ F/cm$^2$) can be evidence of a sufficient coating 115.

The local impedance value, $Z_{local}$, can be determined by forcing current at multiple frequencies onto the pipe 110 and measuring the oscillating potential between the pipe 110 and, preferably, the reference electrode 120. The effective pipe capacitance per unit area can then be estimated.

It is possible to experimentally determine the capacitance per unit of pipe surface for a variety of combinations of pipe materials and soil combinations. The corrosion interface can produce an increase in capacitance such that a substantially corroded surface 150 produces a substantially increased interfacial capacitance relative to the capacitance in the presence of an intact protective coating. For example, it has been experimentally determined that the capacitance of a corroding interface is on the order of 100-300 microfarads per square centimeter in certain soils.

The capacitance of a unit area of pipe 110 surface can be experimentally determined. Thereafter, the total capacitance of a local coating defect 150, or holiday, can be measured in accordance with the present invention. The area of the corroding soil surface can then be determined by simply dividing the total capacitance by the capacitance per unit area.

The reduction of on-pipe current per unit length of pipe 110 and the increase of off-pipe current is largest at locations where there is a holiday 150 or short present. By measuring the rate of change of on-pipe current or off-pipe current, which are complementary, as a function of position along the length of the pipe, local holidays 150 and shorts can be located even when there is a generalized distributed current loss through the protective coating at other regions of the pipe 110. In addition, the properties of the interface between the pipe 110 and the soil electrolyte 140 can be determined in accordance with the present invention for spaced local regions along the pipe 110 for coated 115 and bare pipes. Similarly, the current distribution for spaced locations along the pipe 110, both on-pipe and off-pipe, can be mapped.

Current flowing in the medium surrounding the pipe 110 can then be measured using the probe at each of at least two different frequencies. The condition of the coating 115 can be evaluated in the section using the measured current.

Figure 7:
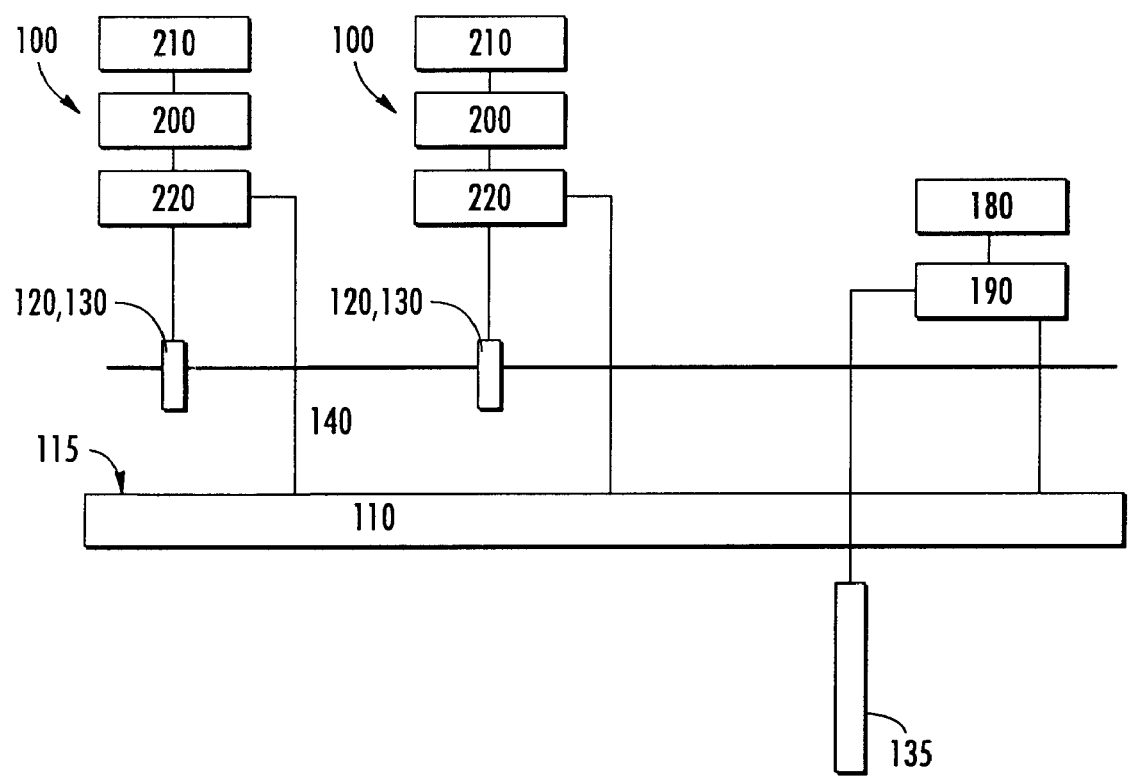
FIG. 7 is a schematic of a system of the present invention, including a device for superimposing a single or multi-sine current on an existing cathodic protection signal, and a device for analyzing impedance that includes several wireless electrodes for measuring local impedance.

One inventive aspect of the invention includes using a signal generator 180 (FIGS. 5-7) to superimpose a multi-frequency sinusoidal (or other AC) signal over the current supplied for cathodic protection 190 (FIGS. 5-7). A probe 100 can include two sensing electrodes 120, 130 and a counter electrode 135, which can be placed in the ground near a section of pipe 110 being analyzed. The sensing electrodes may be numerous shapes, including but not limited to ring-shaped and circular. If the soil 140 resistivity is known, the electrical potential difference between the two sensing electrodes 120, 130 divided by the soil 140 resistivity can be utilized to determine the local current density. An impedance analyzer 200, such as a frequency response analyzer (FRA) or other measuring device can be used to calculate the local impedance response as a function of frequency. Thus, where earlier systems measured the total current flowing in the pipe 110, one or more of the exemplary embodiments of the present invention can measures a local, frequency-dependent impedance. As described below, the local impedance can be analyzed to obtain the capacitance of the section of pipe being analyzed. As noted above, it has been found that coatings 115 in good condition can exhibit a capacitance on the order of $10^{-9}$ F/cm$^2$; whereas, the capacitance of pipes 110 with exposed metal can be on the order of $10^{-5}$ F/cm$^2$. Thus, measurement of capacitance can be sensitive to the localized condition of the coating 115.

ICCP provides a full, wave rectified current. One or more of the exemplary embodiments of the present invention can superpose at least two frequencies of alternating current signals (e.g. a sinusoidal signal) over the current supplied for cathodic protection. A composite signal which includes a large number of frequencies can also be applied to the pipeline 110 for obtaining the measurements described above.

The probes (100) can detect the local current response in the soil 140 adjacent to the pipeline 110.

The current sensing probe 100 can be portable, as shown in FIG. 1. Probe 100 can include a pair of spaced apart electrodes 120, 130, mounted on the ends of a portable A-frame device 100. Various power supply and measurement electronics (not shown) can be incorporated into or utilized with the probe 100. In operation, the electrodes 120, 130 can be inserted in the ground adjacent to pipeline 110. The multi-frequency AC signal can be applied to a pipe 110/counter electrode 135 system and the response can be measured by the potential sensing electrodes 120, 130, which are coupled to the measurement electronics 200, 220 (FIGS. 5-7).

Figure 4:
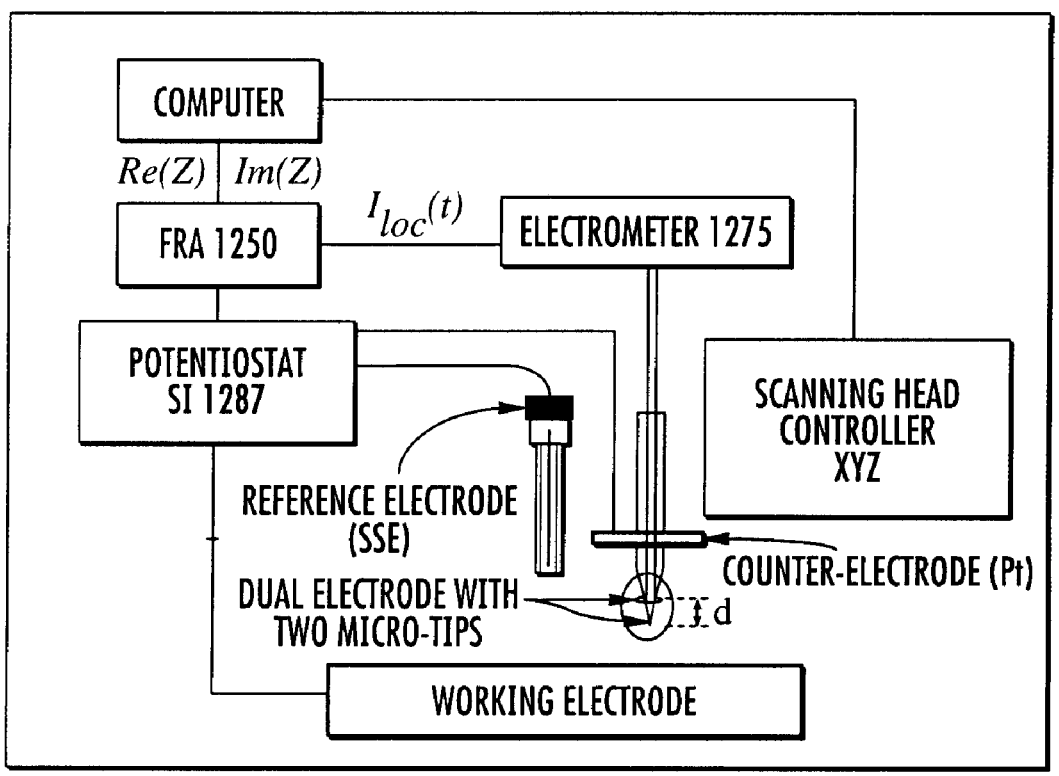
FIG. 4 is a schematic of a probe for measuring local impedance, including a schematic of the components of a device for measuring local impedance.

FIG. 4 shows a probe 110 that can include a pair of spaced apart reference electrodes 120, 130 mounted at the tip of a dual-electrode device. In addition, a block diagram of the components of a device for measuring local impedance is provided.

Figure 2:
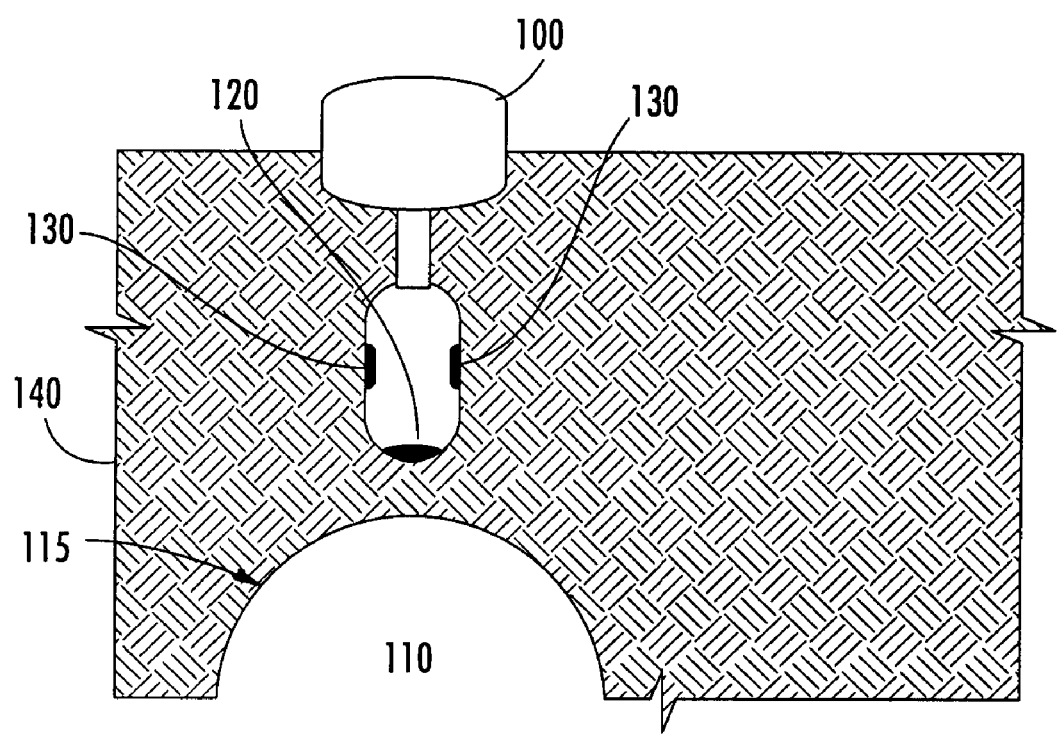
FIG. 2 is a buried probe that includes potential sensing reference and second electrodes.

FIG. 2 shows a probe 100 according to one or more of the exemplary embodiments of the invention that has been buried in the ground. One advantage of the buried probe 100 shown in FIG. 2 is that the data can be updated continuously, whereas the approach using a portable A-Frame 100 shown in FIG. 1 may yield data only when the pipeline is being surveyed, usually no more than once a year.

Only one of the at least two electrodes 120 are shown FIG. 2. Some exemplary electrode 120, 130 choices useful in the present invention include copper/copper sulfate or silver/silver chloride electrodes.

A theoretical treatment is now presented to explain quantitative aspects of the present invention. Although believed to represent the present invention, the claimed invention may be practiced independent of the quantitative aspects provided. The local oscillating current density flowing in the soil 140 between the two reference electrodes 120, 130 adjacent to the pipe 110 will be given by:

$$\tilde{i}_{local} = -\frac{\tilde{\Phi}_{ref,2} - \tilde{\Phi}_{ref,1}}{\rho \delta} \quad (1)$$

where $\Phi_{ref,x}$ is the potential at reference electrode x (potential sensing electrodes), $\delta$ is the distance between the electrodes 120, 130 and $\rho$ is the electrical resistivity of the soil 140 between the two electrodes 120, 130. The local oscillating potential (V) between the pipe metal 110 and the soil 140 can be measured using one of the reference electrodes, preferably the reference electrode 120 closest to the pipe 110 section being analyzed. The local impedance $Z_{local}$ of the series combination of the soil 140 and the corrosion interface can be calculated as:

$$Z_{local} = \frac{\tilde{V} - \tilde{\Phi}_{ref,2}}{\tilde{i}_{local}} \quad (2)$$

Equation (1) may be substituted for the local oscillating current density in equation (2), yielding equation (3).

$$Z_{local} = \delta\rho \frac{\tilde{V} - \tilde{\Phi}_{ref,2}}{\tilde{\Phi}_{ref,1} - \tilde{\Phi}_{ref,2}} = Z_{local,r} + jZ_{local,j} \quad (3)$$

Evaluation of equation (3) requires independent assessment of δ, the distance between reference electrodes 120, 130, and ρ, the electrical resistivity of the soil 140 between the two electrodes 120, 130. For the buried probe 100, such as the one shown in FIG. 2, several electrodes 120, 130 can be used to determine the direction of the current vector. On the soil surface, the dominant component of the current vector can be in the horizontal direction. A frequency response analyzer 200 (FRA) can be used to calculate the local impedance response using Fourier analysis techniques. The value of the local impedance calculated using equations (2) or (3) can depend on frequency. The frequency range and number of frequencies should be sufficient to specify the high-frequency response of the local impedance.

Exemplary Method for Data Interpretation

The method used for data interpretation preferably uses elements disclosed in "Enhanced Graphical Representation of Electrochemical Impedance Data," of the *Journal of the Electrochemical Society* (2006), the disclosure of which is herein incorporated by reference. The method can be automated, but is described through the sequence of steps detailed below.

Figure 8:
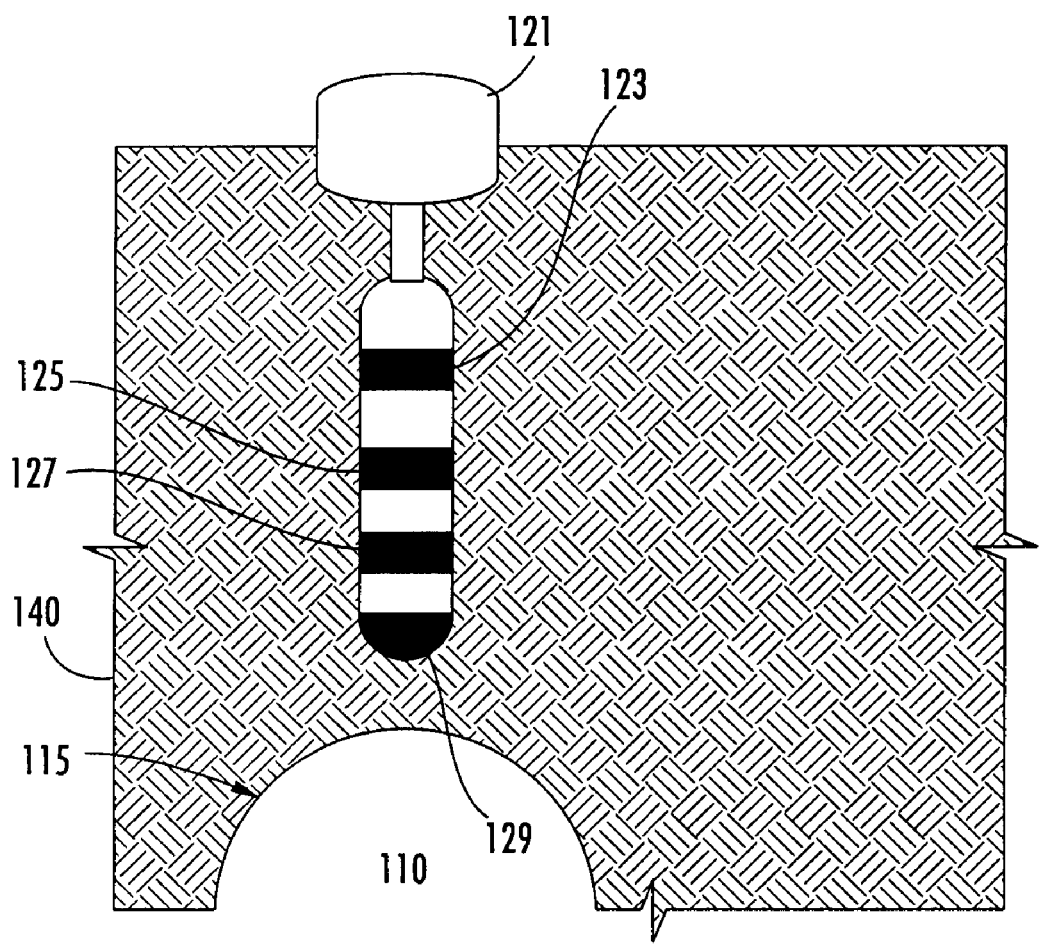
FIG. 8 is a buried probe that includes potential sensing electrodes and current generating electrodes useful for measuring soil resistivity.

First, a measurement using a four-electrode arrangement can be used to obtain a value for the soil resistivity p, allowing calculation of both real ($Z_{local,r}$) and imaginary ($Z_{local,j}$) impedance components. The four-electrodes 123, 125, 127 & 129 can be separate but communicably connected to a processor (not shown), or they may be incorporated into a single four-electrode probe 121, as shown in FIG. 8, or they may be provided in any other configuration that would provide an appropriate arrangement for measuring the soil resistivity. The four-electrode arrangement can be used to provide a type of auto-calibration function The four-electrode measurements are made by taking measurements using a four-electrode arrangement that includes two outer electrodes 123, 129 and two inner, sensing electrodes 125, 127. Generally, the two outer electrodes 123, 129 generate an external current, which may be alternating current (AC) or direct current (DC), while the two inner electrodes 125, 127, detect the resulting potential difference. The potential difference is used to calculate the soil resistivity. In some embodiments, the two inner sensing electrodes can also serve as the reference electrode 120/125 and the second electrode 130/127 for determining the local impedance and assessing the external condition of the pipe 110. The four-electrode probe 121 may be separate from the probe 100, or the probe 100 may be incorporated into the four-electrode probe 121.

Second, the high frequency asymptote for the real impedance yields the value of the electrolyte 140 (e.g. soil) resistance, $R_e$.

$$\lim_{f \to \infty} Z_{local,r} = R_e \quad (4)$$

Third, the slope of the logarithm of the magnitude of the imaginary impedance as a function of the logarithm of the frequency yields a coefficient, α, where:

$$\lim_{f \to \infty} \left[ \frac{d \log |Z_{local,j}|}{d \log f} \right] = -\alpha \quad (5)$$

Fourth, a quantity related to the capacitance of the pipe 110 is calculated as:

$$Q_{eff} = -\lim_{f \to \infty} \left[ \frac{\sin(\frac{\alpha \pi}{2})}{(2\pi f)^\alpha Z_{local,j}} \right] \quad (6)$$

Fifth, the value of the effective pipe capacitance can be estimated from:

$$C_{pipe} = (Q_{eff} R_e^{1-\alpha})^{1/\alpha} \quad (7)$$

The "Enhanced Graphical Representation of Electrochemical Impedance Data" paper, describes the limits calculated in equations (4), (5), and (6) as not depending on the details of the low-frequency response. As noted above, the capacitance per unit area of coatings in sufficient or good condition can be on the order of $10^{-9}$ F/cm$^2$; whereas, the capacitance of exposed metal, i.e. where the coating is missing, can be on the order of $10^{-5}$ F/cm$^2$. Thus, measurements of capacitance made using one or more of the exemplary embodiments of the present invention can be sensitive to the condition of the coating.

Sensitivity to Coating Defects

Figure 3:
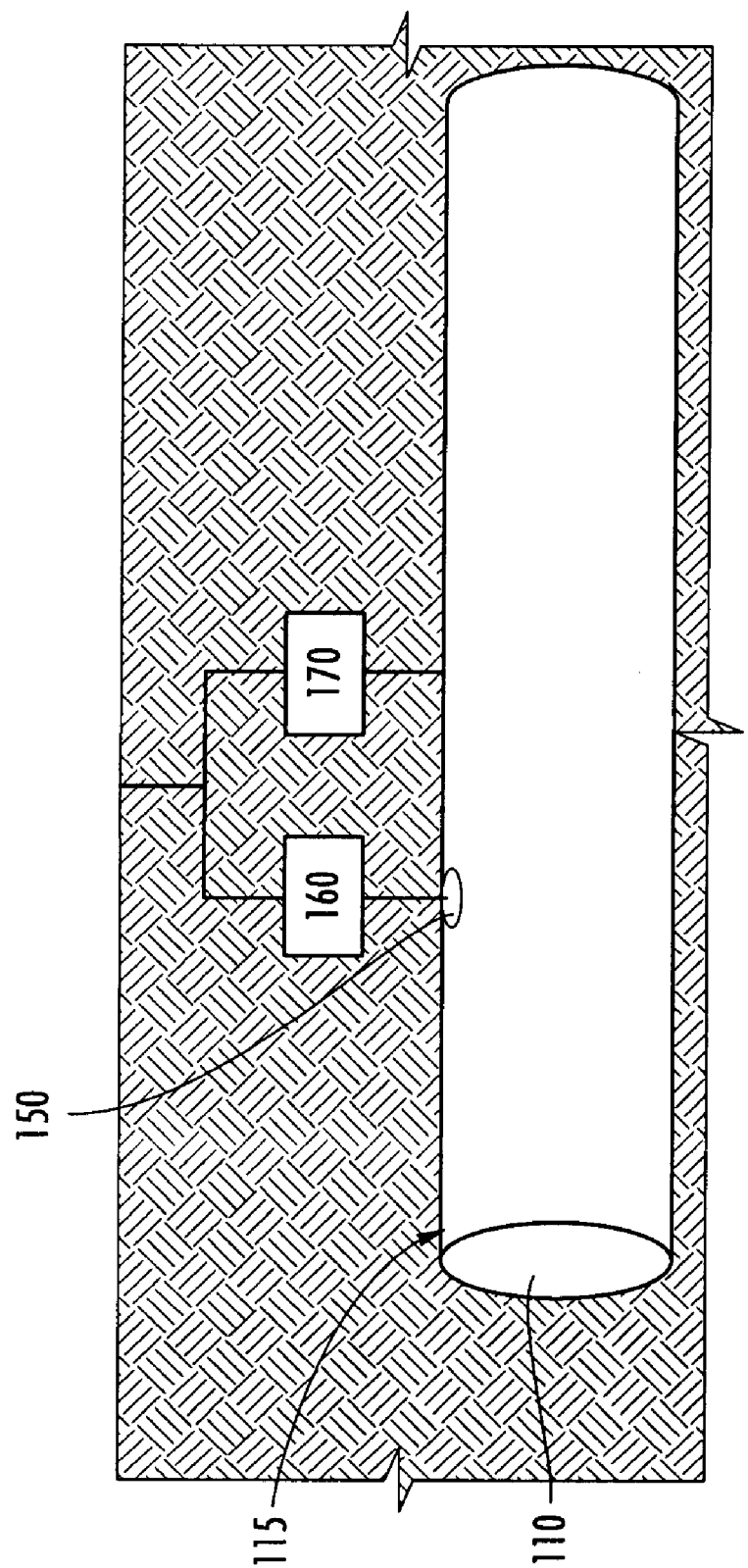
FIG. 3 is a schematic illustration showing impedance of a coated pipe with a localized coating defect.

The impedance of a well and uniformly coated pipe can yield the small value of capacitance associated with good coatings. If a local coating defect 150 exists, as illustrated in FIG. 3, the measured impedance can comprise contributions from both the intact 170 and defective 160 regions. The measured impedance can be expressed as $$Z \frac{1}{\frac{1}{Z_{coated}} \left( \frac{A_{defect}}{A_{coated}} \right) \frac{1}{Z_{defect}}} \quad (8)$$

where $Z_{defect}$ (160) represents the impedance of the region with the coating defect 150 and $Z_{coated}$ (170) represents the impedance of the region with the intact coating. The impedance of the region with an intact coating can be several orders of magnitude larger than the impedance of the defect 160. The measured impedance can therefore be that of the defect so long as the ratio of areas $A_{defect}/A_{coated}$ is not too small. The use of the local impedance measurements can reduce the area of pipe sampled such that the impedance of the coated pipe does not dominate the measured impedance response. The local impedance measurements can be on a millimeter scale, but other scales are also contemplated. An instrument 180 capable of imposing a high-current sinusoidal signal over a broad range of frequencies can be utilized. By measuring local impedance, sensitivity to local pipe 110 conditions can be enhanced.

Advantages of one or more exemplary embodiments of the invention can include that the invention can be utilized while the system is under cathodic protection because the measured current responses are limited to those associated with the multi-frequency signal superimposed on the cathodic protection current. Thus, the pipeline will not need to be depolarized, a process that can take hours to complete.

The local current density can be measured using appropriately spaced (potential sensing) electrodes 120, 130. The spacing between electrodes 120, 130 can be altered as needed to improve sensitivity and the signal-to-noise ratio.

The present disclosure contemplates that the distance between the probe 100 and the pipeline 110 can be based upon a number of factors and/or can be determined by a number of techniques. In one exemplary embodiment, the distance between the probe 100 and pipeline 110 can be based on the dimensions of the pipeline 110, including a diameter or length of the pipeline 110. The ability to obtain accurate impedance responses for distances between a probe 100 and sample, such as a pipeline 110, up to the size of the sample is discussed in more detail in "Experimental Issues Associated with Measurement of Local Electrochemical Impedance" of the *Journal of the Electrochemical Society* of October 2007, the disclosure of which is herein incorporated by reference. In the current environment, this means that accurate impedance measurements can be made for pipelines buried conventional distances underground.

The method for interpretation of the impedance response can be utilized without low-frequency data and without a detailed model of the impedance response. The emphasis on high frequencies, such as in the range of 100 to 10,000 Hz, allows data to be collected in a relatively short period of time. For instance, because high frequency signals can be used in one or more exemplary embodiments of the present invention, each measurement can take less than one second even where multiple sine wave excitations are used for each measurement.

One or more exemplary embodiments of the present invention can employ a mobile A-frame 100 that is currently used to measure potentials above a buried pipeline 110, such as shown in FIG. 1. Using this approach, the operator can position the A-frame 100 in the soil 140, make the measurements, and then reposition the A-frame 100 over a different portion of the pipe 110. Because measurements made using one or more exemplary embodiments of the present invention require less than a second to complete, a protocol similar to the current approach could be used. In another exemplary embodiment, the operator can position the A-frame 100, measure the local impedance spectrum, and then reposition the A-frame 100 for the new measurement.

Prior art systems rely on magnetically-assisted impedance-based systems that require readings both with the CP current and without CP current in order to assess the condition of buried pipeline 110. As described above, one or more exemplary embodiments of the present invention can use an A-frame 100 for taking manual readings. Unlike the prior art, one or more exemplary embodiments of the present invention can be utilized without interruption of the CP current that is protecting the pipeline 110. Furthermore, because no interruption of the CP current is necessary and high frequency current may be used, readings taken using one or more exemplary embodiments of the present invention can be made more quickly than contemporary magnetically-assisted impedance-based systems.

In another embodiment, the measurement approach can also use partially buried probes 100 spaced at intervals along the pipeline 110. A wireless communication system 210 can be used to report sensing data to a central location. The additional sensing capability described below can increase the value of the probe 100 to the pipeline operator.

Systems according to one or more exemplary embodiments of the invention can include additional probes 100 for sensing phenomena other than coating defects 150. For example, chemical probes can be added to detect vapor emissions. In addition to detecting pipe failures, this feature can be useful to detect a leaking valve or flange joint. Such leaks would not necessarily be associated with a coating defect 150. Motion or vibration sensors can be added to detect intrusions, such as unauthorized excavation. Unauthorized intrusions, for instance excavation, by third parties is a major concern for pipeline operators because such intrusions may cause damage to pipelines. The reference electrodes can also be used to detect the steady-state current and electrical potential distributions associated with cathodic protection.

FIGS. 5-7, depict exemplary embodiments of systems of the present invention that can include buried probes 100 for monitoring the condition of a buried pipeline 110. FIGS. 5 & 6 depict wired systems, while FIG. 7 depicts a wireless system. As shown in FIG. 7, the probes 100 of a wireless system can be self-contained probes. Each self-contained probe 100 can include a wireless communications device 210, an impedance analyzer 200, and an electrometer 220 that is connected to the buried pipe 110, the impedance analyzer 200 and an electrode 120, 130. Since the single or multi-sine signal can be generated by a signal generator 180 in a separate location, the power requirements of the self-contained probes 100 can be relatively small. The power requirements can be met by a battery or a combination of a solar panel and a battery. The use of such self-contained probes 100 can greatly simplify the assessment of pipelines 110, including buried pipelines, and enable pipeline operators to monitor the condition of the pipes 110 more frequently and cost effectively.

It is to be understood that while the invention has been described in conjunction with the preferred specific embodiments thereof, that the foregoing description as well as the examples which follow are intended to illustrate and not limit the scope of the invention. For example, the invention can be used for monitoring pipelines 110 in other electrolytic mediums 140, such as sea water. Other aspects, advantages and modifications within the scope of the invention will be apparent to those skilled in the art to which the invention pertains.

I claim:

1. A method for assessment of an external condition of buried pipe, the method comprising:
    disposing a multi-electrode probe having structure for sensing potential comprising at least a first electrode and a second electrode spaced apart from one another in a medium proximate to a section of a pipe to be analyzed, said pipe section having a coating disposed on at least a portion of its length;
    measuring a difference in potential ($V_1$) between said first and second electrodes, and using $V_1$ together with a value for soil resistivity proximate to said pipe section to determine a local current density;
    forcing an alternating current into a circuit comprising said pipe and a bias electrode selected from said first and second electrodes at a plurality of different frequencies and measuring a resulting potential difference ($V_2$) between said pipe and said electrode other than said bias electrode;
    determining a local impedance at said plurality of frequencies from said $V_2$ and said local current density, and
    evaluating a condition of said coating in said section based on said local impedance, or a parameter derived therefrom.

2. The method of claim 1, wherein said pipe is under impressed current cathode protection (ICCP), said forcing step comprising superimposing said alternating current to said pipe section to be analyzed on current supplied for said ICCP.

3. The method of claim 1, further comprising the step of determining a capacitance per unit area of said pipe.

4. The method of claim 1, further comprising the step of measuring the soil resistivity.

5. A method for assessment of a pipe under impressed current cathode protection (ICCP), the method comprising:
    positioning a probe in a medium proximate to a section of the pipe to be analyzed, the section of the pipe having a coating thereon, the probe including at least a first electrode and a second electrode spaced apart from each other;

measuring a difference in potential between the first and second electrodes;

determining a local impedance with respect to the section of the pipe based at least in part on the difference in potential and without interrupting the ICCP; and evaluating a condition of the coating on the section of the pipe based at least in part on the local impedance or a parameter derived from the local impedance.

6. The method of claim 5, further comprising:

measuring a difference in potential $V_1$ between the first and second electrodes;

determining a local current density based at least in part on the difference in potential $V_1$ and a soil resistivity proximate to the section of the pipe;

forcing an alternating current at a plurality of different frequencies into a circuit comprising a bias electrode and the section of the pipe, the bias electrode being one of the first and second electrodes;

measuring a resulting potential difference ($V_2$) between a reference electrode and the section of the pipe, the reference electrode being the other of the first and second electrodes; and determining the local impedance at the plurality of frequencies from the potential difference $V_2$ and the local current density.

7. The method of claim 6, further comprising measuring the soil resistivity.

8. The method of claim 6, wherein the alternating current forced into the circuit is a sinusoidal current superimposed on a protection current of the ICCP.

9. The method of claim 8, wherein the alternating current and the protection current are provided from the same source.

10. The method of claim 5, further comprising determining a capacitance per unit area of the section of the pipe.

11. The method of claim 5, further comprising forcing an alternating current at a plurality of different frequencies into a circuit comprising a bias electrode and the section of the pipe, the bias electrode being one of the first and second electrodes.

12. A system for assessment of a pipe under impressed current cathode protection (ICCP), the system comprising:

a probe having first and second electrodes, the probe being in a medium proximate to a section of the pipe to be analyzed, the section of the pipe having a coating thereon;

a processor in communication with the probe, wherein the processor measures a difference in potential between the first and second electrodes, wherein the processor determines a local impedance with respect to the section of the pipe based at least in part on the difference in potential and without interrupting the ICCP, and wherein the processor evaluates a condition of the coating on the section of the pipe based at least in part on the local impedance or a parameter derived from the local impedance; and a cathodic protection signal generator connected to said pipe and a counter-electrode.

13. The system of claim 12, wherein the processor comprises a frequency response analyzer.

14. The system of claim 12, wherein the processor measures a difference in potential $V_1$ between the first and second electrodes, wherein the processor determines a local current density based at least in part on the difference in potential $V_1$ and a soil resistivity proximate to the section of the pipe;

the system further comprising a signal generator providing an alternating current at a plurality of different frequencies into a circuit comprising a bias electrode and the section of the pipe, the bias electrode being one of the first and second electrodes, wherein the processor (200) measures a resulting potential difference ($V_2$) between a reference electrode and the section of the pipe, the reference electrode being the other of the first and second electrodes, and wherein the processor determines the local impedance at the plurality of frequencies from the potential difference $V_2$ and the local current density.

15. The system of claim 14, wherein the alternating current forced into the circuit is a sinusoidal current superimposed on a protection current of the ICCP.

16. The system of claim 12, wherein the processor determines a capacitance per unit area of the section of the pipe.

17. The system of claim 16, wherein the alternating current and the protection current are provided from the same source.

* * * * *